United States Patent
Uebayashi et al.

(10) Patent No.: US 9,008,402 B2
(45) Date of Patent: Apr. 14, 2015

(54) X-RAY COMPUTED TOMOGRAPHY APPARATUS

(71) Applicants: Kabushiki Kaisha Toshiba, Minato-ku (JP); Toshiba Medical Systems Corporation, Otawara-shi (JP)

(72) Inventors: Yoshinori Uebayashi, Nasushiobara (JP); Chisaka Nagami, Yokohama (JP); Mitsuji Inoue, Yokohama (JP)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/161,141

(22) Filed: Jan. 22, 2014

(65) Prior Publication Data

US 2014/0133624 A1 May 15, 2014

Related U.S. Application Data (62) Division of application No. 12/763,528, filed on Apr. 20, 2010.

(30) Foreign Application Priority Data

May 8, 2009 (JP) ................................. 2009-113571

(51) Int. Cl.
*G06K 9/00* (2006.01)
*A61B 6/03* (2006.01)
(Continued)

(52) U.S. Cl.
CPC ............... *A61B 6/032* (2013.01); *G06T 7/0014* (2013.01); *A61B 6/5205* (2013.01)

(58) Field of Classification Search
USPC ......................................................... 382/131
See application file for complete search history.

(56) References Cited

U.S. PATENT DOCUMENTS 6,493,574 B1 * 12/2002 Ehnholm et al. ............... 600/429
6,959,068 B1 * 10/2005 Sommer ......................... 378/20
(Continued)

FOREIGN PATENT DOCUMENTS

| | | |
|---|---|---|
| JP | 2007-117712 | 5/2007 |
| JP | 2007-159719 | 6/2007 |

(Continued)

OTHER PUBLICATIONS

Office Action issued Jul. 2, 2013 in Japanese Patent Application No. 2009-113571(with English translation).
(Continued)

*Primary Examiner* — Eliza Lam
(74) *Attorney, Agent, or Firm* — Oblon, McClelland, Maier & Neustadt, L.L.P.

(57) ABSTRACT

According to one embodiment, an X-ray computed tomography apparatus comprises an X-ray generating unit, an X-ray detecting unit, a rotating mechanism configured to rotate the X-ray generating unit and the X-ray detecting unit, a reconstruction processing unit configured to reconstruct first images respectively corresponding to volumes, a shift detecting unit configured to detect shifts of an object image due to warp of the top within a reconstruction coordinate system of the reconstruction processing unit, which shifts respectively correspond to the first images, and a control unit configured to move an origin of the reconstruction coordinate system for each of the volumes based on each of the detected shifts and control the reconstruction processing unit to reconstruct second images, which shifts respectively correspond to the volumes from the output from the X-ray detecting unit on the reconstruction coordinate system whose origin has been moved.

5 Claims, 8 Drawing Sheets (51) Int. Cl.
*G06T 7/00* (2006.01)
*A61B 6/00* (2006.01)

(56) References Cited

U.S. PATENT DOCUMENTS 7,324,622 B2 1/2008 Morikawa et al.
2008/0123924 A1 5/2008 Nabatame et al.

FOREIGN PATENT DOCUMENTS

JP 4056922 12/2007
JP 2008-29828 2/2008

OTHER PUBLICATIONS

Murphy et al. "Patterns of Patient Movement During Frameless image-Guided Radiosurgery" Int. J. Radiation Oncology Biol. Phys., vol. 55, No. 5, pp. 1400-1408, 2003.

* cited by examiner

Let Ye0, Ye1, and Ye2 be Y-coordinates of top centers of last images of respective volume Nos, Ys1, Ys2, and Ys3 be Y-coordinates of top centers of first images of respective volume Nos, and Cor(n + 1), Cor(n + 2), and Cor(n + 3) be correction amounts provided for respective volumes.

$$Cor(2) = Ye0 - Ys1$$
$$Cor(3) = (Ye1 - Ys2) + Cor(2)$$
$$Cor(4) = (Ye2 - Ys3) + Cor(3)$$

X-RAY COMPUTED TOMOGRAPHY APPARATUS

CROSS-REFERENCE TO RELATED APPLICATIONS

This application is a divisional application of U.S. application Ser. No. 12/763,528, filed Apr. 20, 2010, which claims the benefit of priority from Japanese Patent Application No. 2009-113571, filed May 8, 2009. The entire contents of the above-identified applications are incorporated herein by reference.

FIELD

Embodiments described herein relate generally to an X-ray computed tomography apparatus.

BACKGROUND

Many of the beds provided for X-ray computed tomography apparatuses use a structure configured to cantilever a top on which an object is placed. This structure allows a reduction in installation space and has superiority in enlarging a work area for an operator. However, the top is inevitably subjected to so-called "warp", that is, deforms downward due to its own weight and the weight of an object.

Conventional methods have used physical and mechanical measures for suppressing the warp of the top, e.g., using a mechanism for supporting the top and improving the rigidity of the top itself. These measures can reduce the warp of the top due to the gravity of the earth but cannot avoid the warp because of the structure configured to cantilever the top.

Owing to this problem, when volume scanning is repeated while the scan position is changed along, for example, the rotation axis of the X-ray tube (Z-axis; approximate to the body axis of an object), an overall image obtained by synthesizing scanned images along the Z-axis has apparent differences in level at the volume scan switching positions. As a consequence, the overall image becomes discontinuous.

In order to solve this problem, a method of measuring the relationship between the position of a top and a warp amount in advance and shifting an image position in accordance with the measurement is often used. These solutions involve a problem of requiring preliminary scanning. The method of solving the problem by shifting images involves a problem of incapability of substantially solving the problem of differences in level (discontinuity) because the warp amount of the top is smaller than the pixel pitch or is not an integer multiple of the pixel pitch.

DETAILED DESCRIPTION

In general, according to one embodiment, an X-ray computed tomography apparatus comprises:

a bed including a cantilevered top;

an X-ray generating unit configured to generate X-rays;

an X-ray detecting unit configured to detect X-rays transmitted through an object placed on the top;

a rotating mechanism configured to rotate the X-ray generating unit and the X-ray detecting unit about a rotation axis;

a reconstruction processing unit configured to reconstruct a plurality of first images respectively corresponding to a plurality of volumes or a plurality of slices arrayed along the rotation axis from an output from the X-ray detecting unit;

a shift detecting unit configured to detect shifts of an object image due to warp of the top within a reconstruction coordinate system of the reconstruction processing unit, which shifts respectively correspond to the plurality of first images, based on the plurality of first images; and a control unit configured to move an origin of the reconstruction coordinate system for each of the volumes or each of the slices based on each of the detected shifts and control the reconstruction processing unit to reconstruct a plurality of second images, upon correction of the shifts of the object image, which shifts respectively correspond to the plurality of volumes or the plurality of slices from the output from the X-ray detecting unit on the reconstruction coordinate system whose origin has been moved.

An X-ray computed tomography apparatus according to a preferred embodiment of the present invention will be described in detail below. Note that X-ray computed tomography apparatuses include various types of apparatuses, e.g., a rotate/rotate-type apparatus in which an X-ray tube and an X-ray detector rotate together around an object, and a stationary/rotate-type apparatus in which many detection elements are arrayed in the form of a ring, and only an X-ray tube rotates around an object. The present invention can be applied to either type. In this case, the rotate/rotate type will be exemplified. In order to reconstruct image data, projection data corresponding to one rotation around an object, i.e., 360°, is required, or (180°+fan angle) projection data is required in the half scan method. The present invention can be applied to either of these reconstruction schemes. The 360° method will be exemplified. As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor such as selenium by X-rays and migration of the electron-hole pairs to an electrode, i.e., a photoconductive phenomenon. As an X-ray detection element, either of these schemes can be used. Recently, with advances toward the commercialization of a so-called multi-tube type X-ray CT apparatus having a plurality of pairs of X-ray tubes and X-ray detectors mounted on a rotating ring, related techniques have been developed. The present invention can be applied to both a conventional single-tube type X-ray CT apparatus and a multi-tube type X-ray CT apparatus. The single-tube type X-ray CT apparatus will be exemplified here.

Figure 1:
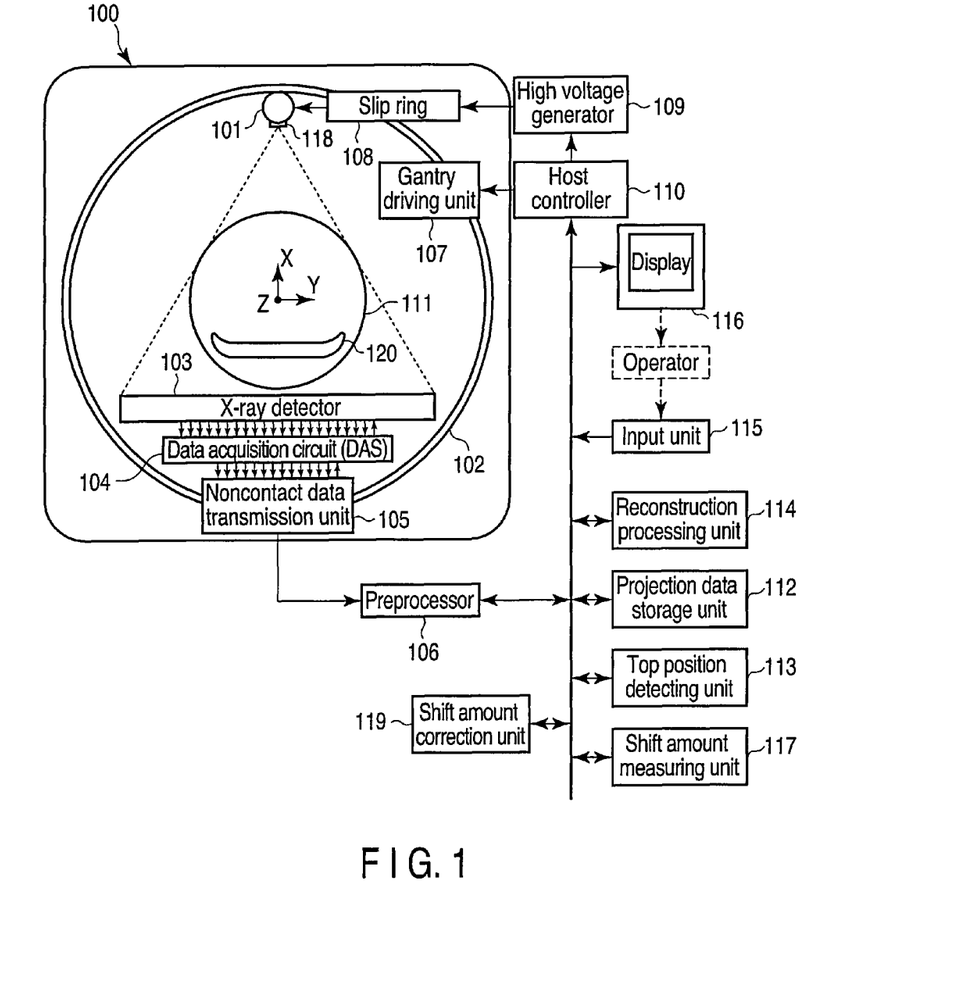
FIG. 1 is a view showing the arrangement of an X-ray computed tomography apparatus according to this embodiment.
Figure 2:
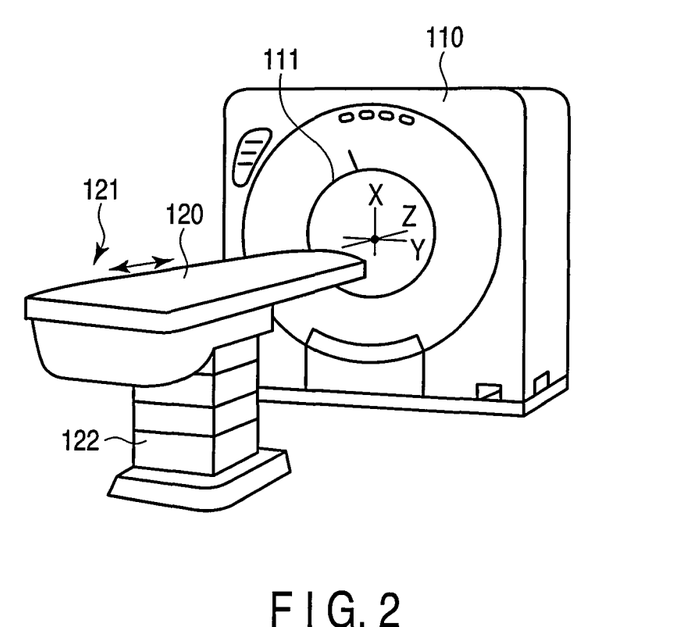
FIG. 2 is a perspective view of a gantry and bed in FIG. 1.

FIG. 1 is a view showing the arrangement of the X-ray computed tomography apparatus according to this embodiment. FIG. 2 is a perspective view of the gantry and bed in FIG. 1. A bed 121 includes a top 120 on which an object is placed. A moving mechanism 122 supports the top 120 so as to make it movable along the Z-axis. The moving mechanism 122 cantilevers the top 120. That is, the top 120 is supported at one end, and the other end of the top 120 is not supported. The other end of the top 120 is free.

A gantry 100 accommodates a rotating support mechanism. The rotating support mechanism includes a rotating ring 102 and a ring support mechanism which supports the rotating ring 102 so as to make it rotatable about the Z-axis. The rotating ring 102 is equipped with an X-ray tube 101. The X-ray tube 101 receives a tube voltage and a tube current from a high voltage generator 109 via a slip ring 108 and generates X-rays from the focal point. A collimator unit 118 is attached to the X-ray irradiation window of the X-ray tube 101. The collimator unit 118 limits X-rays from the X-ray tube 101 to, for example, a rectangular shape. A collimator unit 111 forms X-rays into a cone beam shape (pyramidal shape).

The rotating ring 102 is equipped with an X-ray detector 103. The X-ray detector 103 faces the X-ray tube 101 through the Z-axis. The X-ray detector 103 includes a plurality of X-ray detection elements. Typically, a single X-ray detection element forms a single channel. A plurality of X-ray detection elements are arrayed in a two-dimensional pattern. In addition, a plurality of X-ray detection elements are arranged in a plurality of X-ray detection element arrays each having a plurality of X-ray detection elements arrayed in a line. The X-ray detector 103 may comprise a single X-ray detection element array. In imaging or scanning operation, an object is inserted into a cylindrical imaging area between the X-ray tube 101 and the X-ray detector 103.

A data acquisition circuit 104, which is generally called a DAS (Data Acquisition System), is connected to the output of the X-ray detector 103. The data acquisition circuit 104 is provided with, for each channel, an I-V converter for converting the current signal obtained via each channel of the X-ray detector 103 into a voltage, an integrator for periodically integrating these voltage signals in synchronism with an X-ray irradiation period, an amplifier for amplifying an output signal from the integrator, and an analog/digital converter for converting an output signal from the amplifier into a digital signal.

The data (pure raw data) output from the data acquisition circuit 104 is transmitted to a preprocessor 106 via a noncontact data transmission unit 105 using magnetic transmission/reception or optical transmission/reception. The preprocessor 106 preprocesses this pure raw data. The preprocessing includes, for example, sensitivity nonuniformity correction processing between channels and the processing of correcting an extreme decrease in signal intensity or signal omission due to an X-ray absorber, mainly a metal portion. The data (called raw data or projection data; projection data in this case) output from the preprocessor 106 immediately before reconstruction processing is stored in a projection data storage unit 112 including a magnetic disk, magneto-optical disk, or semiconductor memory in association with data representing view angles at the time of data acquisition.

Note that projection data reflects the intensity of X-rays attenuated by an object. Projection data are repeatedly acquired during one rotation of the X-ray tube 101. A position at which projection data are acquired is called a view. A set of projection data throughout all channels corresponding to the respective views is called a projection data set. The respective view angles are represented by angles in the range of 0° to 360° which represent the respective positions on a circular orbit centered on a rotation central axis Z along which the X-ray tube 101 revolves, with the position of the uppermost position on the orbit being 0°. Each channel data of a projection data set is identified by a view angle, a cone angle, and a channel number.

A reconstruction processing unit 114 reconstructs a plurality of images (three-dimensional images) by the Feldkamp method or the cone beam reconstruction method based on a plurality of projection data sets acquired in the range of 360° or 180°+fan angle. The plurality of three-dimensional images respectively correspond to a plurality of volumes in an almost cylindrical shape which are arrayed along the rotation axis. The reconstruction processing unit 114 also reconstructs a plurality of images (two-dimensional images) associated with a plurality of almost circular slices arrayed along the rotation axis by, for example, the fan beam reconstruction method (also called the beam convolution back projection method). The Feldkamp method is a reconstruction method to be used when projection rays intersect a reconstruction plane like a cone beam. In the Feldkamp method, convolution processing is performed by regarding a projection beam as a fan projection beam on the premise that the cone angle is small, whereas back projection processing is performed along an actual ray in scanning operation. The cone beam reconstruction method is a reconstruction method which corrects projection data in accordance with the angle of a ray relative to a reconstruction plane as a method which suppresses cone angle errors more than the Feldkamp method. For reconstruction processing, a reconstruction coordinate system expressed by three orthogonal axes (x, y, z) corresponding to a real space coordinate system (X, Y, Z) is used.

In practice, projection data corresponding to the respective points on a reconstruction coordinate system are specified by view angles, cone angles, and channel numbers, and the correspondence relationship between the respective points on the reconstruction coordinate system and view angles, cone angles, and channel numbers of the corresponding projection data is determined in advance. The resultant data are stored in a ROM. Changing read control on this ROM will arbitrarily change the correspondence relationship between the respective points on the reconstruction coordinate system and the view angles, cone angles, and channel numbers of the corresponding projection data, thereby substantially implementing the movement of the origin of the reconstruction coordinate system.

This embodiment measures the shift amounts of an object image from a reference position due to the warp of the top 120 within the reconstruction coordinate system (image) of the reconstruction processing unit 114, which shift amounts respectively correspond to a plurality of images, based on a plurality of images respectively correspond to a plurality of volumes or slices. These shift amounts increase depending on the distance from the top supporting position. A shift amount is typically measured based on the top position identified by the top region extracted from each image (first image). However, a shift amount may be measured based on the boundary identified between the object region extracted from an image and the top region. Alternatively, a shift amount may be measured based on, typically, the spinal cord region of an object which is extracted from an image. The following description is based on the assumption that a shift amount is measured based on a top region.

A top position detecting unit 113 extracts a local region having a predetermined size which includes the short-axis central point of the top from a two-dimensional image (tomogram) associated with an x-y plane crossing the top which is generated from a three-dimensional image. The Y-axis of a two-dimensional image corresponds to the warping direction of the top. The top position detecting unit 113 integrates CT values in the X-axis direction corresponding to the short-axis direction of the top for each of all the Y-coordinate points in the local region. Changes in integral value in the Y-axis direction will be referred to as an integral value profile. The top position detecting unit 113 specifies the maximum value of the integral value profile, and detects the corresponding Y-coordinate as a top position on the corresponding slice in the warping direction of the top. The top position may be specified for the position in which the median ((max−min)/2) is shown on the integral value profile or the position in which a predetermined threshold value is shown on the integral value profiles.

A shift amount measuring unit 117 measures the distance between the top position detected by the top position detecting unit 113 and the reference position as a shift amount. Typically, when a plurality of three-dimensional regions discretely or continuously ranging along the rotation axis almost parallel to the body axis of the object are scanned, the shift amount measuring unit 117 sets a reference position at the top position detected from a two-dimensional image in a specific one of the plurality of three-dimensional regions which is nearest to the top supporting position.

A shift amount correction unit 119 substantially corrects the origin position on the reconstruction coordinate system based on the shift amount measured by the shift amount measuring unit 117 under the control of a host computer 110. The reconstruction processing unit 114 then reconstructs a three-dimensional image. The shift amount correction unit 119 moves the origin of the reconstruction coordinate system for each volume or slice based on each shift amount of the top which is measured for each volume or slice. The shift amount correction unit 119 may perform processing almost equivalent to the above processing as follows. The shift amount correction unit 119 corrects the shift of the top position by changing the read address of projection data to be read out from the projection data storage unit 112 to the reconstruction processing unit 114 based on the shift amount measured for each volume or slice under the control of the host computer 110.

Figure 3:
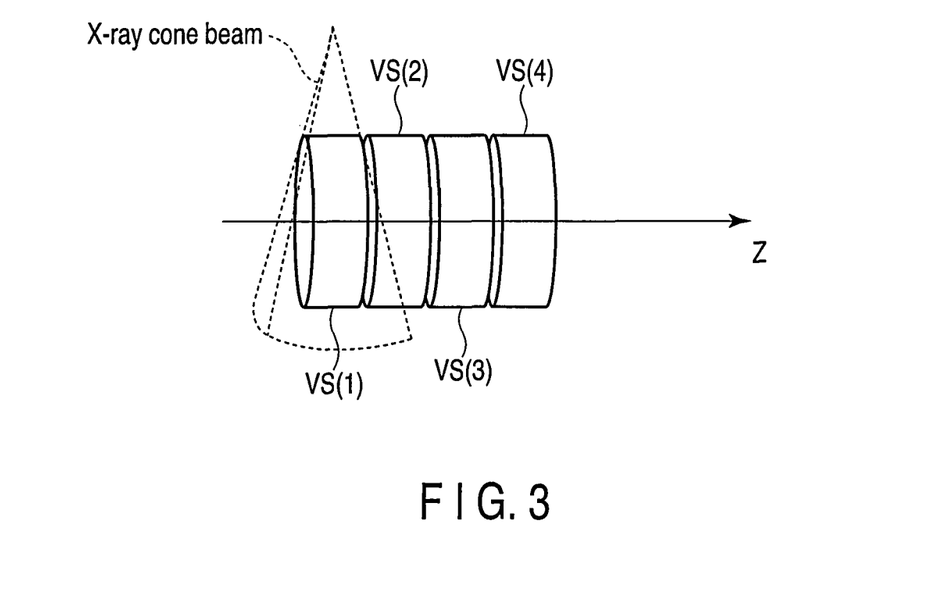
FIG. 3 is a view showing scan regions (three-dimensional regions) preliminarily scanned for top position correction processing in this embodiment.
Figure 4:
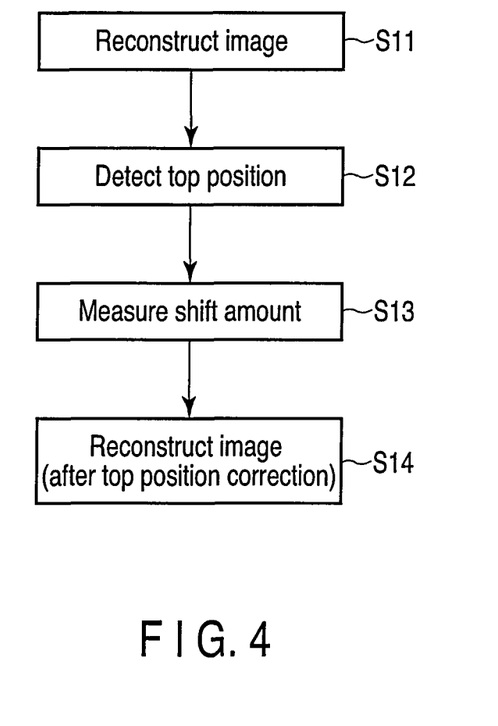
FIG. 4 is a flowchart showing a procedure for top position correction processing according to this embodiment.

FIG. 3 shows a plurality of volume regions (a plurality of three-dimensional regions) VS obtained by volume scanning in this embodiment. FIG. 4 shows a procedure for top position shift correction processing in the embodiment. As shown in FIG. 3, the X-ray tube 101 and the X-ray detector 103 continuously rotate around an object under the control of the host computer 110. During this continuous rotation, conventional scanning is repeated a plurality of number of times while the scan position is discretely displaced. Conventional scanning is performed such that the top is repeatedly moved and stopped, and acquisition of at least a 360° projection data set at each stop position is executed at least once, unlike helical scanning which is performed such that a projection data set is repeatedly acquired while the top continuously moves concurrently with the continuous rotation of the X-ray tube 101 and X-ray detector 103. A projection data set is intermittently repeated while the top is moved by a predetermined distance and stopped. The moving distance of the top per scan is typically matched with the width of the three-dimensional region VS, which can be reconstructed by one scan, in the Z-axis direction. In this case, a plurality of three-dimensional regions VS(1) to VS(4) are continuous. Obviously, the moving distance of the top per scan may be shorter than the width of the three-dimensional region VS in the Z-axis direction. In this case, the plurality of three-dimensional regions VS(1) to VS(4) partially overlap. In addition, the plurality of three-dimensional regions VS(1) to VS(4) have gaps.

In this case, the projection data sets acquired by repetitive conventional scanning are shared by top position correction processing and reconstruction processing for a final diagnosis image, and there is no need to perform scanning for top position correction processing.

Figure 8:
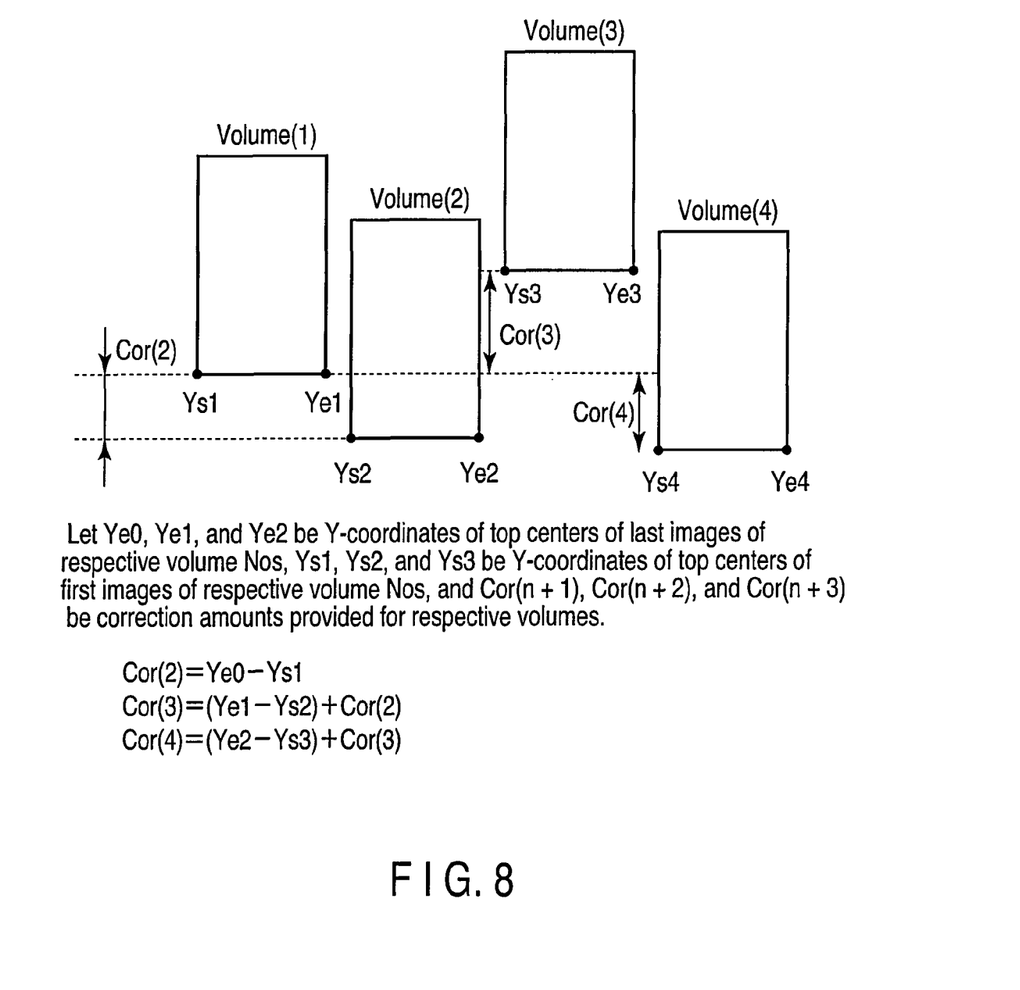
FIG. 8 is a supplementary view for a specific description of a calculation method in the shift amount measurement processing in step S13 in FIG. 4.

When all the projection data sets associated with all the three-dimensional regions VS(1) to VS(4) are completely acquired by repetitive conventional scanning, image reconstruction processing is performed (S11). In the image reconstruction processing, for each of the three-dimensional regions VS(1) to VS(4), the reconstruction processing unit 114 reconstructs three-dimensional image data (volume data) Volume(1) to Volume(4) in almost cylindrical reconstruction ranges (regions equivalent to VS1 to VS4) typically by a cone beam reconstruction method based on projection data sets in the view angle range of 360° or 180°+fan angle, as shown in FIG. 8. This reconstruction processing is performed on the reconstruction coordinate system expressed by the reconstruction processing unit 114 using existing three orthogonal axes (x, y, z).

The top position detecting unit 113 generates two-dimensional images (tomograms) 2Ds(1) to 2Ds(4) associated with slice positions in the three-dimensional regions VS(1) to VS(4) which are nearest to the cantilevering position of the top and two-dimensional images 2De(1) to 2De(4) associated with slice positions in the three-dimensional regions VS(1) to VS(4) which are farthest from the cantilevering position of the top from the volume data Volume(1) to Volume(4) respectively corresponding to the three-dimensional regions VS(1) to VS(4).

According to the above description, in step S11, the reconstruction processing unit 114 reconstructs the volume data Volume(1) to Volume(4) and generates the two-dimensional images 2Ds(1) to 2Ds(4) and 2De(1) to 2De(4) by slice conversion processing for the respective volume data from Volume(1) to Volume(4). However, the reconstruction processing unit 114 may directly reconstruct the two-dimensional images 2Ds(1) to 2Ds(4) and 2De(1) to 2De(4) by the fan beam reconstruction method or the filtered back projection method for slices at predetermined positions in the three-dimensional regions VS(1) to VS(4) without reconstructing the volume data Volume(1) to Volume(4).

Figure 5:
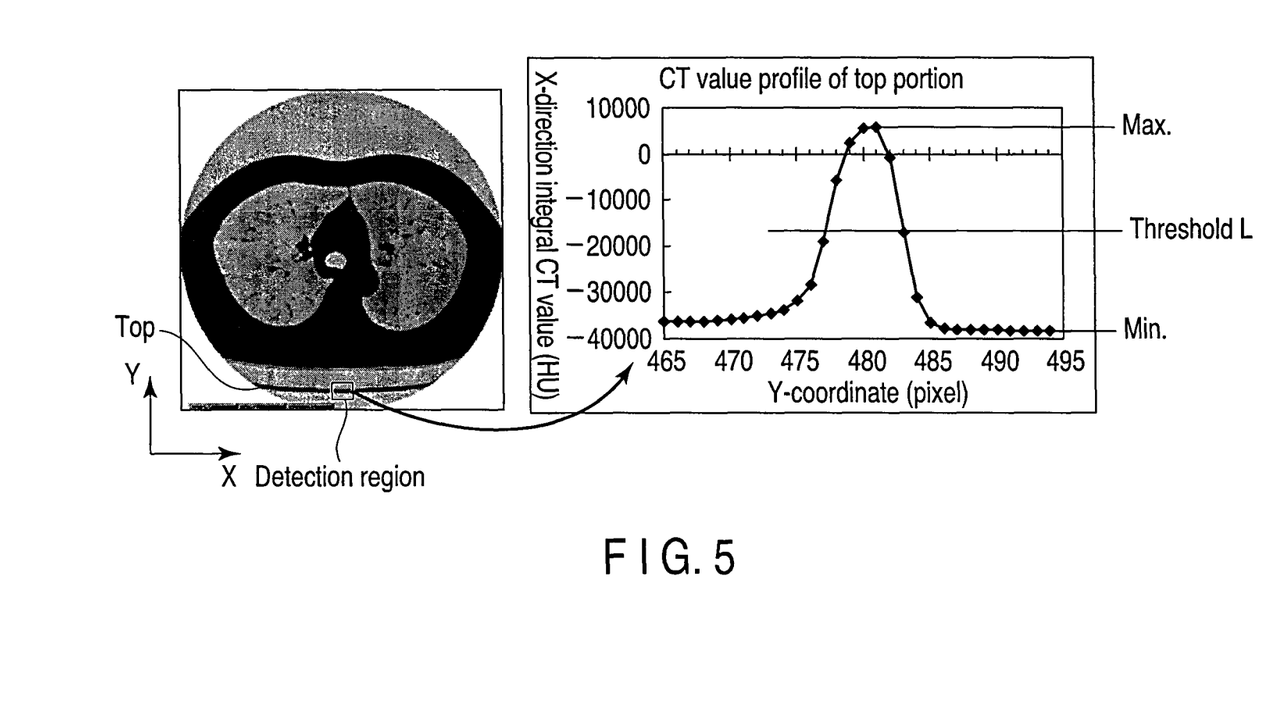
FIG. 5 is a view showing an x-direction profile associated with the integral values obtained by integrating the CT values of a top region in the Y direction in top position detection processing in step S12 in FIG. 4.

The top position detecting unit 113 extracts a top region from each of the two-dimensional images 2Ds(1) to 2Ds(4) and 2De(1) to 2De(4) by threshold processing. As shown in FIG. 5, the top position detecting unit 113 then extracts a local region having a predetermined size which includes the short-axis central point of the extracted top region. The top position detecting unit 113 integrates CT values associated with the X-axis direction corresponding to the short-axis direction of the top for each of all the Y-coordinate points in the local region. FIG. 5 exemplifies changes in integral value in the Y-axis direction as an integral value profile. The top position detecting unit 113 specifies the maximum value of each integral value profile, and detects the Y-coordinates as top positions Ys1 to Ys4 and Ye1 to Ye4 on the corresponding slices in the top warping direction. The top position may be specified for the position in which the median ((max−min)/2) is shown on the integral value profile or the position in which a predetermined threshold value is shown on the integral value profiles.

Figure 6:
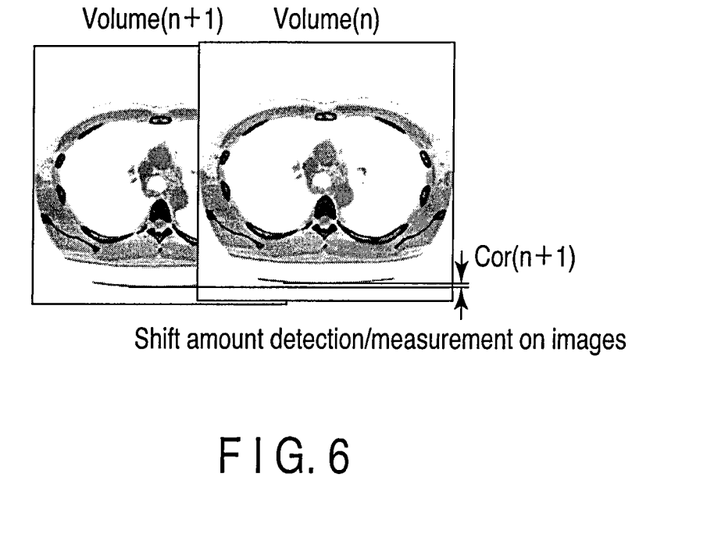
FIG. 6 is a view showing the top position shift amount of a volume (n+1) relative to a volume (n) in shift amount measurement processing in step S13 in FIG. 4.
Figure 7:
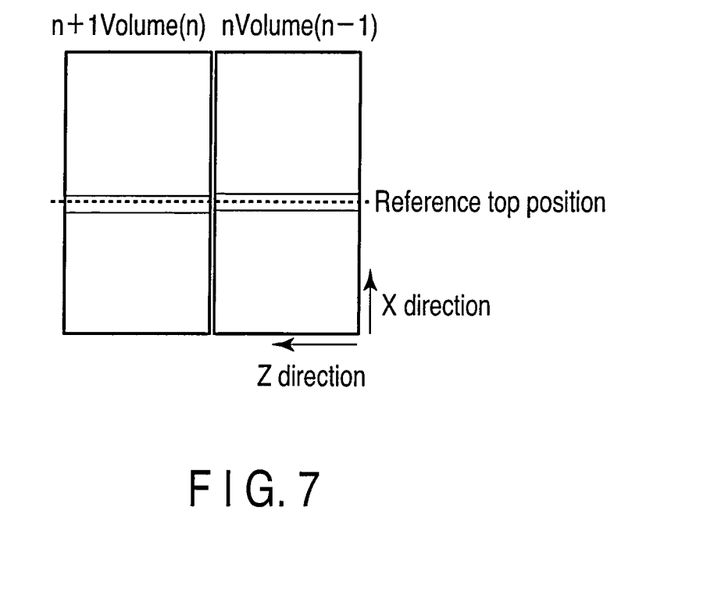
FIG. 7 is a supplementary view of FIG. 6.

The shift amount measuring unit 117 measures the distance between the top position detected by the top position detecting unit 113 and the reference position as a shift amount (S13). Typically, as shown in FIG. 7, a position to be set as a reference position is the top position Ye1 detected from the two-dimensional image 2De(1) in the specific three-dimensional region VS(1), of the plurality of three-dimensional regions, which is nearest to the top supporting position. As shown in FIGS. 6 and 8, the shift amount measuring unit 117 measures the shift amounts of the top positions in the three-dimensional regions VS(2) to VS(4) with reference to the top position in the three-dimensional region VS(1). The shift amount measuring unit 117 calculates shift amounts Cor(2) to Cor(4) of the top positions in the three-dimensional regions VS(2) to VS(4) as follows:

$$Cor(2)=Ye0-Ys1$$

$$Cor(3)=(Ye1-Ys2)+Cor(2)$$

$$Cor(4)=(Ye2-Ys3)+Cor(3)$$

That is, with regard to the adjacent first and second three-dimensional regions, it is possible to eliminate or reduce differences in level at the top positions on a synthesized image obtained by synthesizing long-axis images of X-Z planes in the respective three-dimensional regions by cumulatively adding the shift amount between the top position Ye at the trailing end of the first three-dimensional region and the top position Ys at the leading end of the second three-dimensional region to the initial shift amount Cor(2).

The shift amount correction unit 119 substantially corrects the origin position on the reconstruction coordinate system of the reconstruction processing unit 114 based on the shift amounts Cor(2) to Cor(4) measured by the shift amount measuring unit 117. The reconstruction processing unit 114 then reconstructs a three-dimensional image (S14). More specifically, this operation is equivalent to changing the read address of projection data to be read out from the projection data storage unit 112 to the reconstruction processing unit 114, based on the shift amounts measured by the shift amount measuring unit 117, so as to correct the top position shifts.

Figure 9:
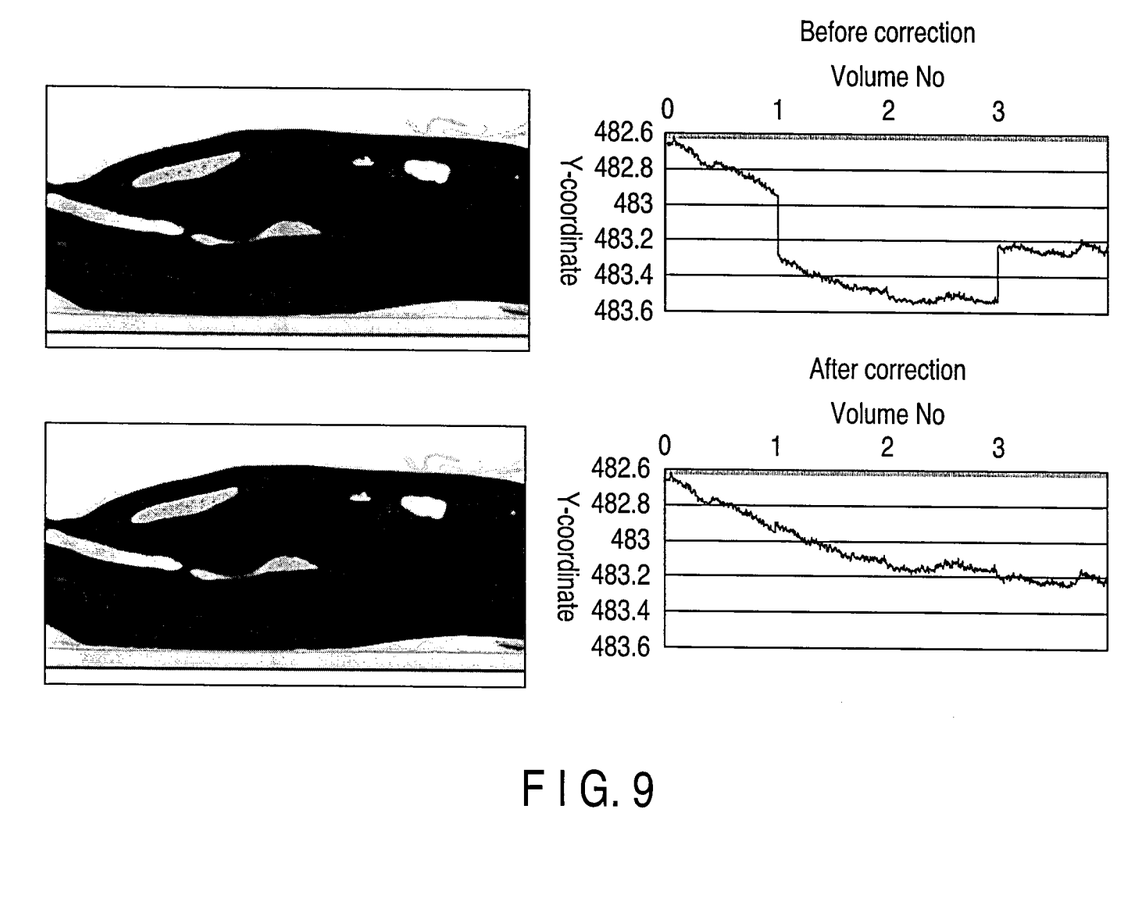
FIG. 9 is a view comparatively showing the continuity of a tomogram in the Z direction after top position correction in this embodiment and the discontinuity of a tomogram in the Z direction before top position correction.

Measuring and correcting top position shifts before and after the respective three-dimensional regions in this manner will generate long-axis images of X-Z planes in the respective three-dimensional regions from four three-dimensional images having undergone top position correction. On the synthesized image obtained by synthesizing these images, it is possible to eliminate or reduce differences in level at the top positions, as shown in FIG. 9, while allowing the warp of the top in each three-dimensional region.

This embodiment is configured to re-execute reconstruction processing by substantially shifting the origin in reconstruction processing instead of an attempt to eliminate shifts by simply shifting initially reconstructed three-dimensional images. Assume that initially reconstructed three-dimensional images are simply shifted. In this case, when a shift amount is smaller than the pixel pitch or does not match an integer multiple of the pixel pitch, the accuracy of positional shift correction deteriorates. This may substantially increase positional shifts. In contrast, this embodiment can avoid such deterioration in accuracy by re-executing reconstruction processing by substantially shifting the origin in reconstruction processing.

In the prior art, there is a limit to the suppression of physical warp, and, for example, an increase in the strength of the top may cause other troubles (artifacts and noise). In addition, since a warp amount is expected to change due to various factors such as a scan range, an object position, and an object weight, it is impossible to prepare a correction table. In addition, these conventional methods require much efforts and time, e.g., scanning twice. In contrast, this embodiment can solve the above problems, eliminate patient position shifts in the respective CT images, and save the user a lot of labor.

According to the above description, the positional shifts between volumes are measured and corrected on a volume basis. However, the positional shifts between central slices of volumes may be measured and corrected on a volume basis.

Figure 10:
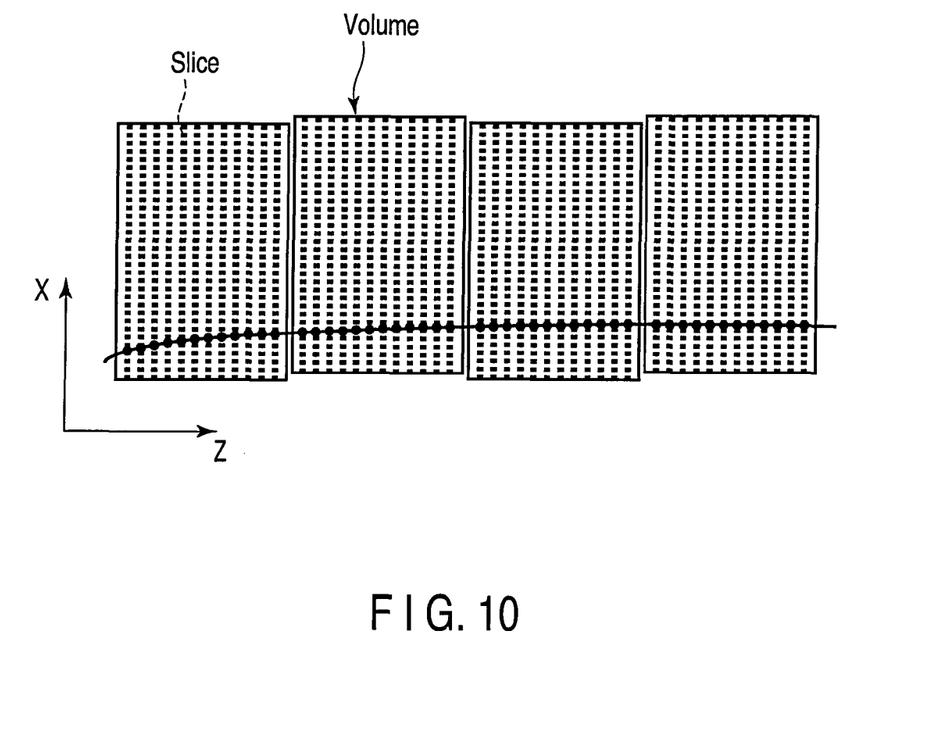
FIG. 10 is a view showing the shift amount of the top position on a slice basis in the shift amount measurement processing in step S13 in FIG. 4.

According to the above description, the positional shifts between volumes are measured and corrected on a volume basis. As shown in FIG. 10, however, the positional shifts between a plurality of slices constituting each volume may be measured and corrected on a slice basis. Alternatively, it is possible to correct positional shifts on a predetermined number of slices basis instead of correcting positional shifts on a slice basis.

In addition, according to the above description, volume scanning has been exemplified as a scanning method. However, shift correction according to this embodiment can also be applied to helical scanning. In this case, positional shifts are corrected every slice or every a predetermined number of slices.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray computed tomography apparatus, comprising:
    a bed configured to movably cantilever a top on which an object is placed;
    an X-ray tube configured to generate X-rays;
    a detector configured to detect X-rays generated by the X-ray tube and transmitted through the object;
    a gantry configured to rotate the X-ray tube and the detector about a predetermined rotation axis; and
    processing circuitry configured to
        reconstruct a plurality of three-dimensional images ranging along the rotation axis based on an output of the detector;
        extract a top region of the top on which the object is placed from each of the plurality of three-dimensional images;
        measure a shift amount between a front end position of the top region on one of adjacent three-dimensional images of the plurality of three-dimensional images and a rear end position of the top region on another one of the adjacent three-dimensional images; and
        generate a synthesized image on which the top regions are continuous by synthesizing the plurality of three-dimensional images while performing position correction based on the shift amount.

2. The X-ray computed tomography apparatus according to claim 1, wherein a two-dimensional image associated with an end slice of each of the plurality of three-dimensional images is generated from said each of the plurality of three-dimensional images.

3. The X-ray computed tomography apparatus according to claim 2, wherein a position at which an integral value obtained by integrating CT values in a short-axis direction of the top regarding an approximate center region of the top region on the two-dimensional image exhibits a maximum value is detected as the top position.

4. The X-ray computed tomography apparatus according to claim 1, wherein the X-ray tube generates X-rays in a cone beam shape, and the detector is an area detector.

5. The apparatus according to claim 1, wherein the rear end position is adjacent to the front end position.

\* \* \* \* \*